United States Patent [19]
Akasaka et al.

[11] Patent Number: 5,089,408
[45] Date of Patent: Feb. 18, 1992

[54] GLUTATHIONE PEROXIDASE GENE AND PROCESS FOR PRODUCTION OF THE GENE PRODUCT

[75] Inventors: Masami Akasaka; Akiko Kubota; Junzo Mizoguchi, Japan; Sakae Satoh, all of Shizuoka, Japan

[73] Assignee: Toyo Jozo Kabushiki Kaisha, Shizuoka, Japan

[21] Appl. No.: 368,982

[22] Filed: Jun. 15, 1989

[30] Foreign Application Priority Data

Jun. 15, 1988 [JP] Japan .................................. 63-147884

[51] Int. Cl.$^5$ ........................ C12N 15/53; C12N 9/08; C12N 15/00
[52] U.S. Cl. .................................. 435/192; 435/252.3; 435/240.1; 536/27
[58] Field of Search .............. 536/27; 435/69.1, 172.3, 435/240.1, 252.3, 192

[56] References Cited

PUBLICATIONS

Mullenbach et al., NAR, vol. 15, p. 5484, 1987.
Sukenaga et al., NAR, vol. 15, p. 7178, 1987.
Chambers et al., EMBO, vol. 5, pp. 1221–1227, 1986.
Takahashi et al., Archives of Biochem. & Biophys., vol. 256, pp. 677–686, 1987.
"Primary Structure of Human Plasma Glutathione Peroxidase Deduced from cDNA Sequences", *Journal of Biochemistry*, vol. 108, 1990, by K. Takahashi et al., pp. 145–148.

*Primary Examiner*—Richard A. Schwartz
*Assistant Examiner*—S. L. Nolan
*Attorney, Agent, or Firm*—Young & Thompson

[57] ABSTRACT

DNA which encodes at least a polypeptide containing glutathione peroxidase activity and having an amino acid sequence from the N-terminal to the C-terminal of the formula:

Ala—Phe—Ile—Ala—Lys—Ser—Phe—Tyr—Asp—Leu—Ser—
—Ala—Ile—Ser—Leu—Asp—Gly—Glu—Lys—Val—Asp—
—Phe—Asn—Thr—Phe—Arg—Gly—Arg—Ala—Val—Leu—
—Ile—Glu—Asn—Val—Arg—Ser—Leu—***—Gly—Thr—Thr—
—Thr—Arg—Asp—Phe—Thr—Gln—Leu—Asn—Glu—Leu—
—Gln—Cys—Arg—Phe—Pro—Arg—Arg—Leu—Val—Val—
—Leu—Gly—Phe—Pro—Cys—Asn—Gln—Phe—Gly—His—
—Gln—Glu—Asn—Cys—Gln—Asn—Glu—Glu—Ile—Leu—
—Asn—Ser—Leu—Lys—Tyr—Val—Arg—Pro—Gly—Gly—
—Gly—Tyr—Gln—Pro—Thr—Phe—Thr—Leu—Val—Gln—
—Lys—Cys—Glu—Val—Asn—Gly—Gln—Asn—Glu—His—
—Pro—Val—Phe—Ala—Tyr—Leu—Lys—Asp—Lys—Leu—
—Pro—Tyr—Pro—Tyr—Asp—Asp—Pro—Phe—Ser—Leu—
—Met—Thr—Asp—Pro—Lys—Leu—Ile—Ile—Trp—Ser—Pro—
—Val—Arg—Arg—Ser—Asp—Val—Ala—Trp—Asn—Phe—
—Glu—Lys—Phe—Leu—Ile—Gly—Pro—Glu—Gly—Glu—
—Pro—Phe—Arg—Arg—Tyr—Ser—Arg—Thr—Phe—Pro—
—Thr—Ile—Asn—Ile—Glu—Pro—Asp—Ile—Lys—Arg—Leu—
—Leu—Lys—Val—Ala—Ile wherein * * * is selenocystein, is produced by culturing transformant host cells which possess extraneous DNA encoding a polypeptide with glutathione peroxidase activity in a medium containing selenium, and separating a thus-produced polypeptide with glutathione peroxidase activity from the cultured mass.

8 Claims, 5 Drawing Sheets

FIG. 1

$X_1$ Ala Phe Ile Ala Lys Ser Phe Tyr Asp
Leu Ser Ala Ile Ser Leu Asp Gly Glu Lys
Val Asp Phe Asn Thr Phe Arg Gly Arg Ala
Val Leu Ile Glu Asn Val Arg Ser Leu Sec
Gly Thr Thr Thr Arg Asp Phe Thr Gln Leu
Asn Glu Leu Gln Cys Arg Phe Pro Arg Arg
Leu Val Val Leu Gly Phe Pro Cys Asn Gln
Phe Gly His Gln Glu Asn Cys Gln Asn Glu
Glu Ile Leu Asn Ser Leu Lys Tyr Val Arg
Pro Gly Gly Gly Tyr Gln Pro Thr Phe Thr
Leu Val Gln Lys Cys Glu Val Asn Gly Gln
Asn Glu His Pro Val Phe Ala Tyr Leu Lys
Asp Lys Leu Pro Tyr Pro Tyr Asp Asp Pro
Phe Ser Leu Met Thr Asp Pro Lys Leu Ile
Ile Trp Ser Pro Val Arg Arg Ser Asp Val
Ala Trp Asn Phe Glu Lys Phe Leu Ile Gly
Pro Glu Gly Glu Pro Phe Arg Arg Tyr Ser
Arg Thr Phe Pro Thr Ile Asn Ile Glu Pro
Asp Ile Lys Arg Leu Leu Lys Val Ala Ile
$X_2$

FIG. 2  DNA Sequence Name (1): hGP-A    (55-621)
Comment:

```
         10         20         30         40         50         60
GCTTTCATTG CCAAGTCCTT CTATGACCTC AGTGCCATCA GCCTGGATGG GGAGAAGGTA
         70         80         90        100        110        120
GATTTCAATA CGTTCCGGGG CAGGGCCGTG CTGATTGAGA ATGTGCGTTC GCTCTGAGGC
        130        140        150        160        170        180
ACAACCACCC GGGACTTCAC CCAGCTCAAC GAGCTGCAAT GCCGCTTTCC CAGGCGCCTG
        190        200        210        220        230        240
GTGGTCCTTG GCTTCCCTTG CAACCAATTT GGACATCAGG AGAACTGTCA GAATGAGGAG
        250        260        270        280        290        300
ATCCTGAACA GTCTCAAGTA TGTCCGTCCT GGGGGTGGAT ACCAGCCCAC CTTCACCCTT
        310        320        330        340        350        360
GTCCAAAAAT GTGAGGTGAA TGGGCAGAAC GAGCATCCTG TCTTCGCCTA CCTGAAGGAC
        370        380        390        400        410        420
AAGCTCCCCT ACCCTTATGA TGACCCATTT TCCCTCATGA CCGATCCCAA GCTCATCATT
        430        440        450        460        470        480
TGGAGCCCTG TGCGCCGCTC AGATGTGGCC TGGAACTTTG AGAAGTTCCT CATAGGGCCG
        490        500        510        520        530        540
GAGGGAGAGC CCTTCCGACG CTACAGCCGC ACCTTCCCAA CCATCAACAT TGAGCCTGAC
        550        560        570
ATCAAGGCGC TCCTTAAAGT TGCCATA
```

FIG. 3A    CGCTCATAAGTGGGCTCAGGCCTCTCTGCGGGCTCACTCTGCGCTTCACC

ATGGCTTTCATTGCCAAGTCCTTCTATGACCTCAGTGCCATCAGCCTGGATGGGGAGAAG
MetAlaPheIleAlaLysSerPheTyrAspLeuSerAlaIleSerLeuAspGlyGluLys

GTAGATTTCAATACGTTCCGGGGCAGGGCCGTGCTGATTGAGAATGTGCGTTCGCTCTGA
ValAspPheAsnThrPheArgGlyArgAlaValLeuIleGluAsnValArgSerLeu***

GGCACAACCACCCGGGACTTCACCCAGTTCAACGAGCTGCAATGCCGCTTTCCAGGCGC
GlyThrThrThrArgAspPheThrGlnLeuAsnGluLeuGlnCysArgPheProArgArg

CTGGTGGTCCTTGGCTTCCCCTTGCAACCAATTTGGACATCAGGAGAACTGTCAGAATGAG
LeuValValLeuGlyPheProCysAsnGlnPheGlyHisGlnGluAsnCysGlnAsnGlu

GAGATCCTGAACAGTCTCAAGTATGTCCGTCCTGGGGGTGGATACCAGCCACCTTCACC
GluIleLeuAsnSerLeuLysTyrValArgProGlyGlyGlyTyrGlnProThrPheThr

CTTGTCCAAAAATGTGAGGTGAATGGGCAGAACGAGCATCCTGTCTTCGCCTACCTGAAG
LeuValGlnLysCysGluValAsnGlyGlnAsnGluHisProValPheAlaTyrLeuLys

GACAAGCTCCCCCTACCCTTATGATGACCCATTTTCCCTCATGACCGATCCCAAGCTCATC
AspLysLeuProTyrProTyrAspAspProPheSerLeuMetThrAspProLysLeuIle

ATTTGGAGCCCTGTGCGCCGCTCAGATGTGGCCTGAACTTTGAGAAGTTCCTCATAGGG
IleTrpSerProValArgArgSerAspValAlaTrpAsnPheGluLysPheLeuIleGly

FIG. 3B

```
       490        500        510        520        530        540
CCGGAGGGAGAGCCCTTCCGACGCTACAGCCGCCACCTTCCAACCATCAACATTGAGCCT
ProGluGlyGluProPheArgArgTyrSerArgThrPheProThrIleAsnIleGluPro 550        560        570
GACATCAAGCGCCTCCTTAAAGTTGCCATATAGATGTGAACTGCTCAACACACAGATCTC
AspIleLysArgLeuLeuLysValAlaIle***

CTCATCCATCCAGTCCTGAGGAGCCTTAGGATGCAGCATGCCTTCAGGAGACACTGCTGG

ACCTCAGCATTCCCTTGATATCAGTCCCCTTCACTGCAGAGCCTTGCCTTTCCCCTCTGC

CTGTTTCCTTTTCCTCTCCCAACCCTCTGGTTGGTGATTCAACTTGGGCTCCAAGACTTG

GGTAAGCTCTGGGCCTTCACAGAATGATGGCACCTTCCTAAACCCTCATGGGTGGTGTCT

GAGAGGCGTGAAGGGCCTGGAGCCACTCTGCTAGAAGAGACCAATAAAGGGCAGGTGTGG

AAAAAAAAAAAAAAAAAAAAAAAAAAAAAA
```

FIG. 4

$E^p$: PROMOTER OF EARLY GENE IN SV40
Ap: AMPICILLIN RESISTANT
O : ORIGIN OF REPLICATION

GLUTATHIONE PEROXIDASE GENE AND PROCESS FOR PRODUCTION OF THE GENE PRODUCT

FIELD OF THE INVENTION

This invention relates to a novel deoxyribonucleic acid encoding the genetic information of glutathione peroxidase, a transformant containing the said DNA, a polypeptide obtained by expressing the said genetic information of the said DNA with said transformant, and a process for its production.

BACKGROUND OF THE INVENTION

Glutathione peroxidase is an enzyme which catalyzes a reaction of two moles of glutathione and one mole of hydrogen peroxide to form two moles of glutathione-oxide and two moles of water, and is found in mammalian tissues and organs such as liver, kidney, heart, lung, red blood cells and blood plasma. [Flohe, L. et al., FEBS Letters, 32: 132-134 (1973)]It plays an important role in the treatment of biological peroxide by catalyzing the reduction by two electrons of lipid-peroxide with glutathione. Glutathione peroxidase is a protein containing selenium which has the amino acid selenocystein (Sec) in its active center. According to a study on a cloned mouse glutathione peroxidase gene, the opal codon, TGA, of the corresponding ribonucleic acid sequence (RNA), which is in general a termination codon, in this enzyme codes for selenocystein (Sec) [EMBO J., Vol. 5, No 6, pp. 1221-1227 (1986)].

A human-type glutathione peroxide (hereinafter sometimes designated h-GSHPx) has been separated from erythrocyte and blood plasma, and has been known to be a homotetramar, in which the molecular weight of the four erythrocyte type subunits thereof is each 20,600 and that of the blood plasma type subunits is each 21,500. [Archives of Biochemistry and Biophysics, Vol. 256, (2): 677-686 (1987) and The Journal of Biological Chemistry, Vol. 262 (36): pp. 17398-17403 (1987)]

h-GSHPx's derived from erythrocytes, liver and kidney are believed to be identical due to their strong immunological cross reactivity and similar subunit molecular weight of approximately 20,600. The h-GSHPx gene is quite homologous to the mouse GSHPx gene, however the mouse h-GSHPx gene product shares little immunological similarity with h-GSHPx derived from blood plasma. Hence at present more than two kinds of h-GSHPx are known.

These h-GSHPx's were cloned from a c-DNA library of m-RNA isolated from liver and kidney cells, and their gene structure has been determined. [Nucleic Acids Research, Vol. 15, No. 13, pp. 5484 (1987), ibid., Vol. 15, No. 17, pp. 7178 (19870]. Although h-GSHPx protein of blood plasma has been isolated, its gene has not been cloned.

OBJECTS OF THE INVENTION

An object of the present invention is to provide a novel DNA sequence which is translatable into at least the amino acid sequence of a polypeptide comprising glutathione peroxidase having a novel structure.

Another object of the present invention is to provide a transformant which possesses the DNA which has a base sequence coding for an amino acid sequence of a polypeptide comprising glutathione peroxidase which is extraneous for the host.

A further object of the present invention is to provide a polypeptide comprising h-GSHPx expressed in the amino acid sequence hereinabove.

A still further object of the present invention is to provide a process for the production of h-GSHPx which comprises culturing the transformant carrying DNA which has a base sequence encoding a polypeptide comprising h-GSHPx hereinabove which is extraneous for the host, in a medium containing selenium, expressing the genetic information of the said DNA, and isolating a polypeptide comprising h-GSHPx from the cultured medium.

SUMMARY OF THE INVENTION

The h-GSHPx gene of liver and kidney cells has been cloned and its structure elucidated. We have successfully obtained the novel h-GSHPx gene by deriving the different type of h-GSHPx gene from a c-DNA library of human liver, and have elucidated its structure.

Figure 3A:
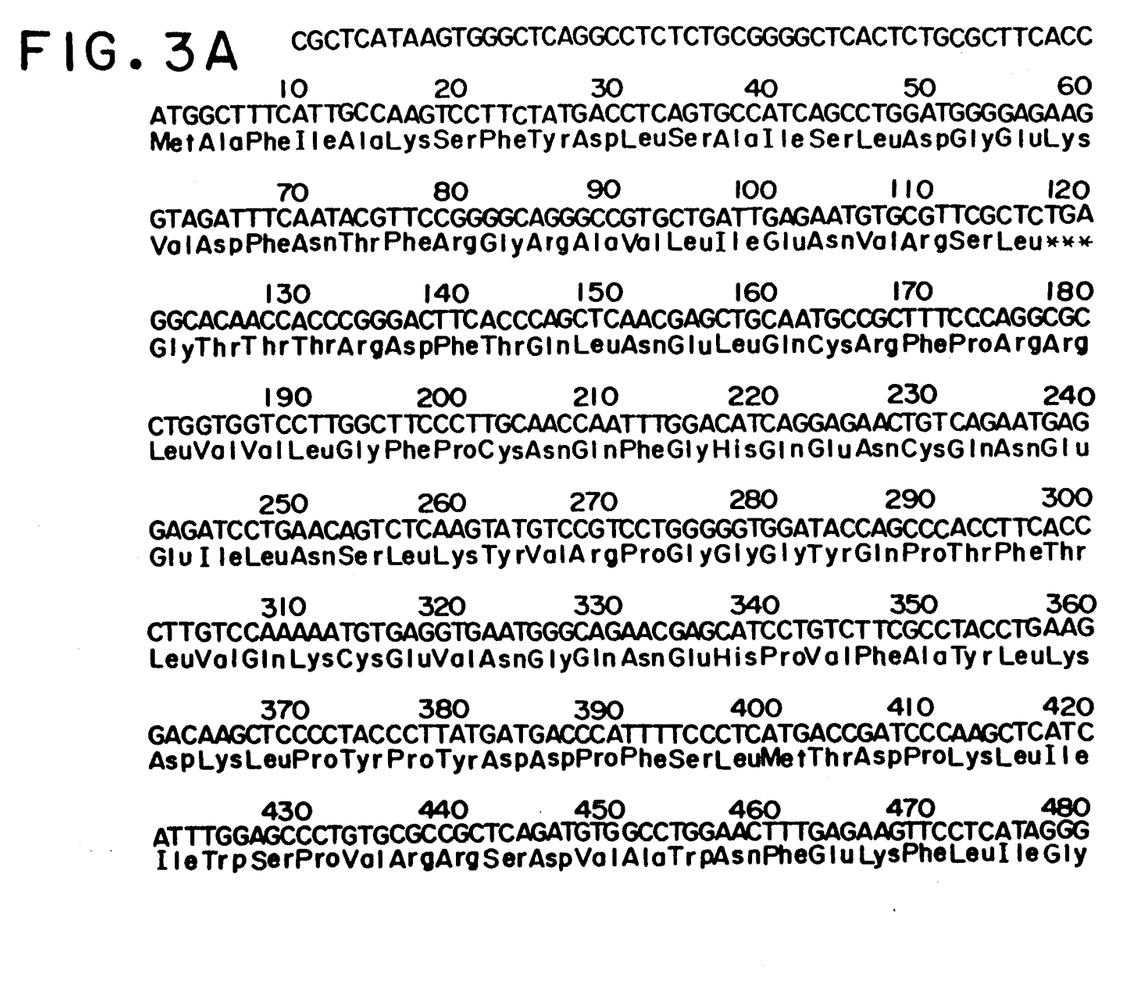
FIGS. 3A and 3B: polydeoxyribonucleic acid and coding region of amino acids including glutathione peroxidase gene.
Figure 3B:
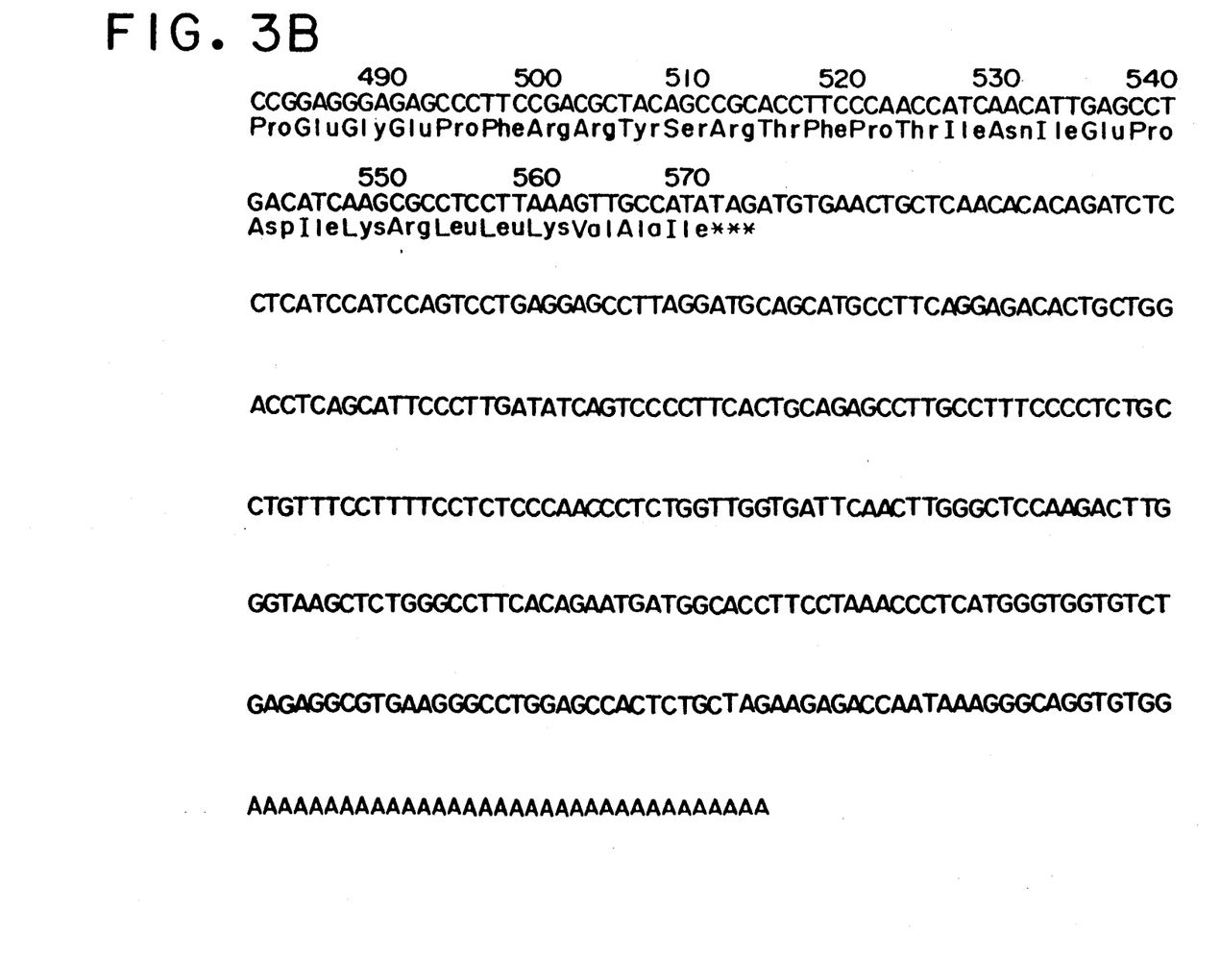

The h-GSHPx gene consists of 951 base pairs of DNA and an extended 3' poly-A tail as shown in FIGS. 3A and 3B. The open reading frame of this sequence extends from an initiation condon to a termination condon, and is translatable into a polypeptide at the structure of h-GSHPx comprising 189 amino acids of the formula, Ala—Phe—Ile—Ala—Lys—Ser—Phe—Tyr—Asp—Leu— [1]
    Ser—Ala—Ile—Ser—Leu—Asp—Gly—Glu—Lys—Val—
    Asp—Phe—Asn—Thr—Phe—Arg—Gly—Arg—Ala—Val—
    Leu—Ile—Glu—Asn—Val—Arg—Ser—Leu—***—Gly—
    Thr—Thr—Thr—Arg—Asp—Phe—Thr—Gln—Leu—Asn—
    Glu—Leu—Gln—Cys—Arg—Phe—Pro—Arg—Arg—Leu—
    Val—Val—Leu—Gly—Phe—Pro—Cys—Asn—Gln—Phe—
    Gly—His—Gln—Glu—Asn—Cys—Gln—Asn—Glu—Glu—
    Ile—Leu—Asn—Ser—Leu—Lys—Tyr—Val—Arg—Pro—
    Gly—Gly—Gly—Tyr—Gln—Pro—Thr—Phe—Thr—Leu—
    Val—Gln—Lys—Cys—Glu—Val—Asn—Gly—Gln—Asn—
    Glu—His—Pro—Val—Phe—Ala—Tyr—Leu—Lys—Asp—
    Lys—Leu—Pro—Tyr—Pro—Tyr—Asp—Asp—Pro—Phe—
    Ser—Leu—Met—Thr—Asp—Pro—Lys—Leu—Ile—Ile—
    Trp—Ser—Pro—Val—Arg—Arg—Ser—Asp—Val—Ala—
    Trp—Asn—Phe—Glu—Lys—Phe—Leu—Ile—Gly—Pro—
    Glu—Gly—Glu—Pro—Phe—Arg—Arg—Tyr—Ser—Arg—
    Thr—Phe—Pro—Thr—Ile—Asn—Ile—Glu—Pro—Asp—
        Ile—Lys—Arg—Leu—Leu—Lys—Val—Ala—Ile wherein * * * is selenocystein.

The coding region of this gene is 61.0% homologous in nucleotide sequence and 66.1% homologous in amino acid sequence with the known h-GSHPx of human liver. [Nucleic Acids Research, Vol. 15, No. 17, pp. 7178 (1987)], and hence it is a novel gene. Furthermore, according to comparative studies of gene expression by Northern blot technique with two known kinds of h-GSHPx genes, the h-GSHPx gene of the present invention was found to code for the majority of h-GSHPx RNA found in liver cells whereas the previously known h-GSHPx gene was responsible for expression of a minor isomer thereof.

Figure 2:
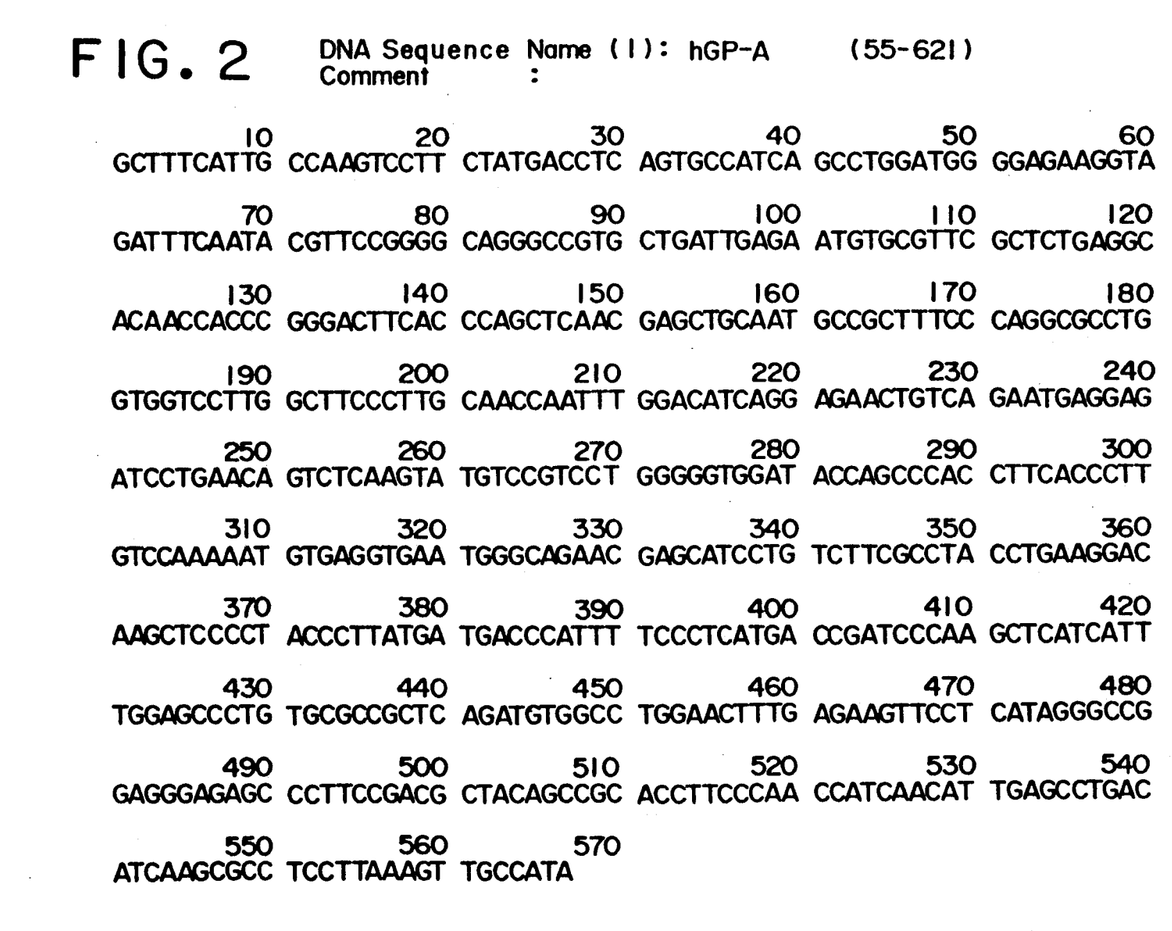
FIG. 2: base sequence of glutathione peroxidase gen of the present invention.

We have also obtained a polypeptide comprising h-GSHPx of the formula [1]hereinabove, which is translated in a 5' to 3' manner from base No. 1 to No. 567 of FIG. 2, and that it is a novel polypeptide having an opal codon (TGA) which encodes selenocystein.

Furthermore by genetic engineering techniques, we have created the transformant which contains the novel h-GSHPx DNA sequence which is translatable into the amino acid sequence of the polypeptide comprising h-GSHPx of the present invention. We have also established a mass production process using the transformant containing the novel h-GSHPx DNA to obtain large quantities of h-GSHPx.

DETAILED DESCRIPTION OF THE INVENTION

The h-GSHPx gene of the present invention can be derived from a commercially available human liver c-DNA library or a similar library obtained by integrating a DNA fragment reverse transcribed from liver mRNA into a phage or cosmid vector. For example, powdered human liver tissue can be homogenized with guanidium solution. A suspension is passed several times through 18·½ gauge syringe needle to cleave high molecular DNA into fragments and is layered on a 5.7M cesium chloride solution, and centrifuged at 36,000 rpm at 25° C. overnight. The sedimentate is washed with a small amount of ethanol and dissolved in water with 0.3M of added sodium acetate, then 2.5 volumes of ethanol are added thereto. The re-sedimented total RNA is collected by centrifugation, dissolved in 0.5 M NaCl solution, heated at 65° C. for 5 mins., and thereafter immediately cooled. The solution is passed through a column of oligo(dT)-cellulose and poly-A containing RNA is retained by annealing with oligo(dT). Single strand DNA is synthesized using the poly-A(+) RNA as template by using reverse transcriptase. The complimentary DNA is synthesized by DNA polymerase I after RNase H digestion of the RNA. The EcoRI site in the gene is methylated by EcoRI methylase, and the termini are blunt ended by $T_4$ DNA polymerase. EcoRI linker DNA is ligated to both terminals and the DNA is digested with the restriction enzyme EcoRI, simultaneously removing the excessive added linker, then fractionated by electrophoresis. Fractionated polynucleotide is linked to phage vector λgtll which had been previously digested with EcoRI. This c-DNA library consisting of the gtll vector in which the DNA fragments prepared originally from liver mRNA are integrated into a suitable host organism.

The above c-DNA library is screened with a synthesized DNA probe which includes the TGA selenocystein codon referred to in the known GSHPx gene. For example, a synthetic oligonucleotide including a codon TGA for selenocystein, which codes for the amino acid sequence of No. 31(Ser) to No. 57(Asn) from N-terminal(Cys), in known mouse GSHPx gene is used as a probe for screening.

A host cell, Escherichia coli LE392, infected with λgtll vector of the c-DNA library, is cultured on an agar medium to lyse grown cells. Phage is absorbed on a nylon membrane filter placed on a surface of the lysate medium. The filter is treated with alkali to denature the DNA, neutralized and the DNA fixed by heating at 80° C. for 2 hours. The thus-treated filter is kept at 42° C. for 60 mins. in a prehybridization solution (e.g. 5×Denhart solution, 5×SSC (sodium chloride +sodium citrate), 50 mM sodium phosphate pH 6.5, 0.1% SDS (sodium dodecyl sulfate), 250 μg/ml exogenous DNA and 50% formamide). The $^{32}P$-labelled DNA probe described hereinbefore is added to the solution and hybridized at 42° C. overnight. The treated filter is washed three times in 2×SSC and 0.1% SDS at room temperature and successively, at 50° C. 0.1×SSC and 0.1% SDS at 50° C. and air-dried. The filter is exposed to x-ray film and positive plaques can be identified from the auto radiograph. Plaques are recovered, and re-inoculated onto agar plate to ensure isolation of a single colony of phage.

The host cells infected with the isolated pure phage are cultured in a liquid medium overnight, centrifuged and the supernatant recovered.

20% polyethylene glycol containing 2.5M NaCl is added thereto, and the material is ice-cooled and centrifuged at 15,000 rpm for 20 mins. The precipitate is dissolved in SM (0.1M NaCl, 8mM $MgSO_4$, 50mM Tris-HCl pH 7.5 and 0.02% gelatin solution) and extracted with phenol to extract the DNA. The thus-extracted DNA is digested with restriction enzyme EcoRI and purified to isolate the h-GSHPx gene, which is subcloned by ligation into the EcoRI site in a plasmid pUC 118. Thus the plasmid pUC 118-GPA comprising the h-GSHPx gene inserted at the EcoRI site of the plasmid pUC 118, is prepared. In the subcloning hereinabove, the plasmid pUC 118 can be replaced by a plasmid having a preferred restriction enzyme site, for example a plasmid for the host bacteria belonging to Escherichia coli, such as pBR 322, pBR 325, pACYC 184, pUC 12, pUC 18 or pUC 19, and a plasmid for the host bacteria. Bacillus subtilis, such as pUB 110 or pC 194.

Furthermore, in order to confirm expression of h-GSHPx activity by the plasmid pUC 118-GPA, a suitable expression vector is assembled. Preferred examples of the expression vector are plasmid pINI and pINIII for the host bacteria Escherichia coli such a E. coli DHl, E. coli HB 101, E. coli MV 1304, E. coli W3110 or E. coli C 600; plasmid pTUB 218 and pTUB 285 for Bacillus subtilis; plasmid pAM 82 for Saccharomyces cerevisae; and a virus vector which expresses an extraneous gene inserted downstream of the late promoter of SV 40 virus, such as plasmid pSVL (Pharmacia Co.) or plasmid pSV 2-dhfr (BRL Co.) for animal cells such as primate kidney (COS) cells, Chinese hamster ovary (CHO) cells or CHO-dhfr (dehydrofolate reductase defective) cell-line. These expression vectors can be digested by restriction enzymes and any sites thereof added or cut off to accommodate the h-GSHPx gene.

Expression of h-GSHPx activity, for example in CHO cells, can be confirmed as follows. DNA fragments containing h-GSHPx gene are obtained by digesting and splitting the plasmid pUC 118-GPA with a suitable restriction enzyme and inserting this DNA into the pSV 2-dhfr vector by replacing part of the dhfr region. By these procedures, DNA fragments of the h-GSHPx gene are linked downstream of the early gene promoter of SV 40, to obtain the expression vector plasmid pSV2-GPA-dhfr.

The thus-prepared expression vector is transferred into the host cells by the known process for example a calcium phosphate method in which the expression vector obtained by the above procedure is transferred into COS cells or CHO cells, to obtain the transformant.

The transformant, such as CHO cells holding the plasmid pSV2-GPA-dhfr, can be cultured in a medium containing selenium by a conventional cell culture method for animal cells such as CHO cells. For examples, the transformant cells are spread in a culture medium, such as in petri dishes, containing the modified Dulbecco-Eeagle MEM medium +10% fetal bovine serum +0.01–0.05 μM selenious acid, at approximately $10^4$ cells/cm$^2$ and cultured at 30°–37° C. for 2–6 days. Cultured cells are collected and crushed, then the aqueous supernatant, in which h-GSHPx activity is confirmed, is treated by conventional known methods for enzyme isolation and purification to recover h-GSHPx. A solution containing h-GSHPx can be treated by preferred methods such as vacuum concentration, membrane concentration, salting out with ammonium sulfate or sodium sulfate, or fractionation precipitation using a water-miscible organic solvent such as methanol, ethanol or acetone. The precipitate containing h-GSHPx is purified, if required, by any of various methods such as dialysis, ion-exchange chromatography, adsorption chromatography or gel filtration. The thus-purified h-GSHPx is stored by lyophilization.

The plasmid pUC 118-GPA containing h-GSHPx gene has been carried in an *Escherichia coli* DHI transformant designated as a strain *Escherichia coli* DH1 pUC 118-GPA, and deposited as FERM BP-1903 under the Budapest Treaty in The Fermentation Research Institute, Japan.

A gene consisting of 951 base pairs extended from the poly-A tail contains the h-GSHPx coding region as shown in FIGS. 3A and 3B and can be obtained by using the above plasmid. The said gene has an open reading frame including an initiation codon (ATG at positions Nos. 1–3) and a termination codon (TAG at positions Nos. 571–573). The base sequence of the above gene was determined by direct sequencing.

Figure 1:
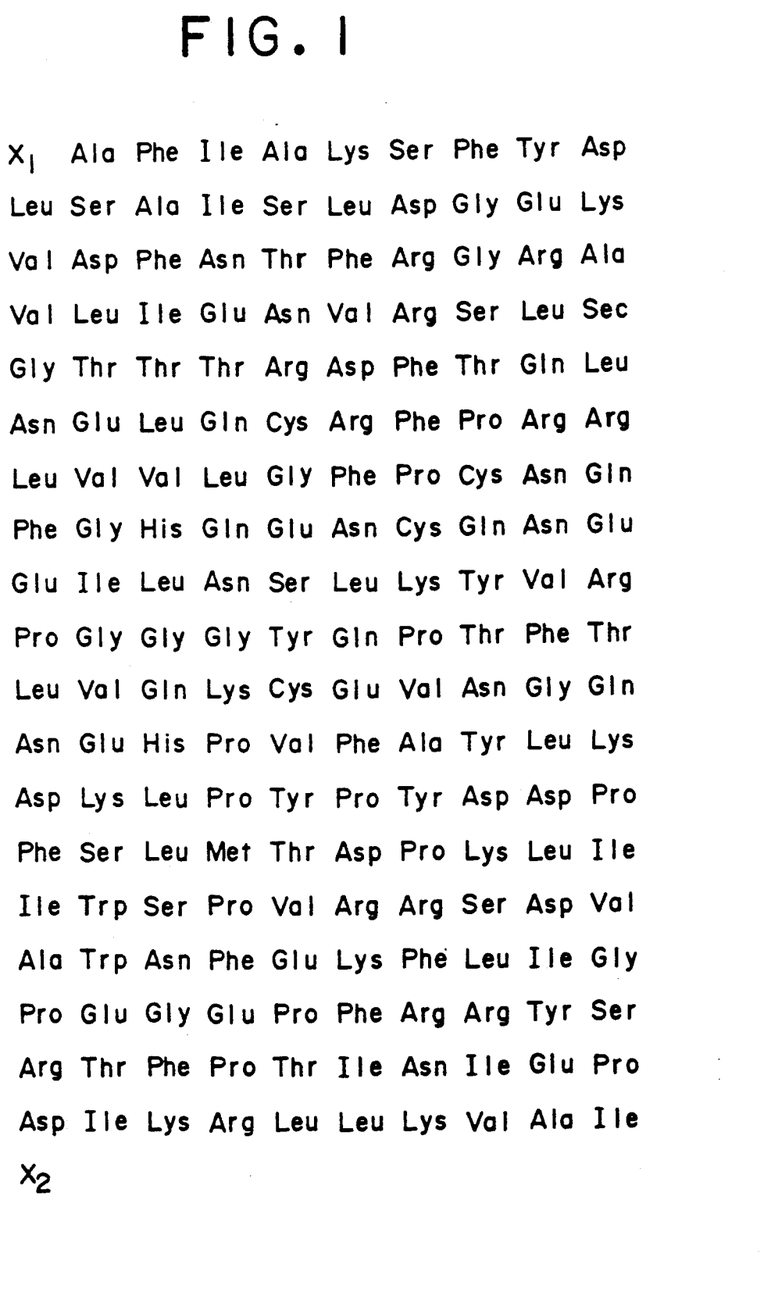
FIG. 1: amino acid sequence of glutathione peroxidase of the present invention.

The h-GSHPx codes for at least a polypeptide consisting of 189 amino acids shown in FIG. 1. In FIG. 1, Xl can optionally be hydrogen, acetyl, methionine or a signal peptide including methionine. The said structure gene shows homology for the known h-GSHPx of human hepatocytes [Nucleic Acids Res., Vol. 15, No. 17, pp. 7178 (1987)] with 61.0% of nucleotide sequence and 66.1% of amino acid sequence, and it is a novel gene. A base sequence for the polypeptide consisting of h-GSHPx in FIG. 1 is illustrated as from base No. 1 to No. 567 from the 5'-terminal in FIG. 2, and has an opal codon (TGA) which codes for selenocystein, and it also is a novel gene. The codon upstream from GCT at the 5'-terminal in FIG. 2 can be any codon which codes for an amino acid and can have more than one codon coding amino acids, at the 5'-terminal, and is preferably ATG or a polydeoxyribonucleic acid corresponding to a signal peptide. A downstream codon from ATA at the 3'-terminal can be a termination codon or a codon coding an amino acid or peptide. Furthermore, when in the 3'-terminal region more than one codon which codes amino acid or peptide is present, an additional termination codon is preferably provided at the 3'-terminal side.

An amino acid sequence of polypeptide of h-GSHPx, which is produced by expressing the novel DNA coding an amino acid sequence of polypeptide consisting of h-GSHPx, can be determined by the base sequence of said DNA. An amino acid sequence at the N-terminal of the polypeptide consisting of h-GSHPx is determined by a liquid phase protein sequencer (Beckman Co.) and is confirmed as being identical at the N-terminal thereof with an amino acid sequence determined from its DNA base sequence. Accordingly, the polypeptide consisting of h-GSHPx of the present invention has an amino acid sequence at least illustrated as the formula [I]hereinbefore.

A transformant can also be obtained by transforming the expression vector into a preferred host microorganism instead of the CHO cells hereinabove. Examples of transformant microorganisms are those belonging to genus *Escherichia coli*, which is cultured in a medium for expressing h-GSHPx. Cultivation can be performed in a liquid culture medium, and a submerged aeration culture is preferred for industrial production.

A conventional medium for culturing microorganisms can preferably be used. For the carbon sources, assimilable carbon sources such as glucose, sucrose, molasses, glycerol, starch hydrolyzate or the like can preferably be used. Assimilable nitrogen sources such as corn steep liquor, soybean powder, peptone, meat extract, yeast extract, casein hydrolyzate, ammonium sulfate, ammonium chloride or the like can be used. Various inorganic salts such as phosphates, chlorides, carbonates, sulfates or nitrate salts of sodium magnesium, calcium, potassium, iron, manganese, zinc or 0.05–10 μM in the culture medium.

The culturing temperature can be selected within the range for growth of microbial cells and production of h-GSHPx, and is preferably 20°–42° C. for *E. coli*. The culturing time can be altered depending on conditions and is terminated when the h-GSHPx production is substantially complete, and is usually 12–72 hours.

To separate h-GSHPx from the cultured medium, the whole cultured mass is used. When the h-GSHPx is an endoenzyme, the cultured mass is filtered or centrifuged to collect the cells, which are disrupted by treatment with mechanical means or enzymes such as lysozyme. Furthermore, if necessary, h-GSHPx can be solubilized by adding a chelating reagent and a surfactant to extract the enzyme.

The enzyme can be purified by the conventional means as hereinbefore illustrated.

The activity of the h-GSHPx is determined for example as follows. A solution of h-GSHPx 10 μl is mixed with a solution (0.98 ml) containing 0.1M Tris-HCl buffer (pH 8.0), 0.2 mM reduced NADP, 0.5 mM EDTA, 2 mM glutathione and 1 unit of glutathione reductase, to which is added butanol peroxide (Bu OOH), and the decreasing absorbance of reduced NADP at 340 nm by oxidation thereof is spectrophotometrically measured at 37° C. By this means expression and production of h-GSHPx can be confirmed.

Abbreviations of amino acid, peptide, nucleic acid and others are illustrated according to commonly used notation. All amino acids shown herein are in the L-isometric form.

The following examples illustrate the present invention but are not to be construed as limiting.

EXAMPLE 1

Human liver 10g was powdered in liquid nitrogen, homogenized in 6M guanidine isothiocyanate (40 ml) and passed through an 18.5 G injection needle to reduce its viscosity by splitting high molecular DNA. The homogenate was layered on a 1/3 volume solution of 5.7M cesium chloride and 0.1M EDTA (pH 7.5), and centrifuged at 35,000 rpm at 25° C. for 18 hours. The precipitate was washed with small amount of ethanol to remove excess cesium chloride. The precipitate dissolved in water (1 ml) was centrifuged after adding 1/10 volume of 3M sodium acetate and 2.5 volumes of ethanol, and the precipitate was collected and dried in vacuo to obtain crude RNA (5 mg).

The precipitate dissolved in water (1.5 ml), heated at 65° C. for 5 mins. was immediately cooled and there was added thereto a solution (1.5 ml) of 40 mM Tris-HCl (pH 7.6), 1.0 M NaCl, 2 mM EDTA and 0.2% SDS. The solution was adsorbed on a column of oligo (dT) cellulose (Pharmacia Co.) (75 mg) equilibrated with 20 mM Tris-HCl (pH 7.6), 0.5M NaCl, 1 mM EDTA and 0.1% SDS, and washed with the same solution (10 ml). RNA except poly (A)+RNA was eluted with a solution (5 ml) of 20 mM Tris-HCl (pH 7.6), 0.1M NaCl, 1 mM EDTA and 0.1% SDS.

Poly (A)+RNA was eluted with a solution of 10 mM Tris-HCl (pH 7.5), 1 mM EDTA and 0.05% SDS, and the first eluted fraction (1 ml) was collected. A 1/10 volume of 3M sodium acetate and 2.5 volumes of ethanol were added thereto, and the mixture was allowed to stand at $-20°$ C. overnight, centrifuged at 15,000 rpm for 30 mins. to collect the precipitate and lyophilized. Poly (A)+RNA (50 μg) was obtained.

EXAMPLE 2

Poly (A)+RNA obtained in Example 1 was dissolved to 1 μg/ml in water. The solution (5 μl) transferred into a micro-tube was heated at 65° C. for 5 mins. and immediately cooled. 50 mM Tris-HCl (pH 8.3), 10 mM $MgCl_2$, 140 mM KCl, 10 mM dithiothreitol and 2 mM d NTPs (equivalent mixture of dATP, dGTP, dCTP and dTTP), oligo(dT) (5 μg) (Pharmacia Co.) and reverse transcriptase (1.5 unit) (Takara Shuzo Co.) were added thereto. The total volume of the mixture was increased to 20 μl and the mixture was incubated at 42° C. for one hour. 80 mM Tris-HCl (pH 7.5), 200 mM KCl, 10 mM $MgCl_2$, 25 μg/ml BSA and RNas H (Takara Shuzo Co.) (60 units) and DNA polymerase I (Boehringer Mannheim Co.) (5 units) were added to the incubated mixture above which increased its total volume to 50 μl. The mixture was reacted at 120° C. for one hour and then at 22° C. for one hour. 0.25M EDTA (20 μl) and 10% SDS (10 μl) were added to stop the reaction, and an equal amount of phenol-chloroform was added; then the mixture was centrifuged at 10,000 rpm for 5 mins. The aqueous layer was collected and an equal amount of 4M ammonium acetate and twice the volume of ethanol were added thereto. The mixture was centrifuged at 15,000 rpm for 15 mins., and the precipitate was collected and dried in vacuo. 100 mM Tris-HCl (pH 8.0), 10 mM EDTA, 80 μM S-adenocylmethionine, 100 μg/ml BSA and 2 units of EcoRI methylase (Promegabiotech Co.) were added thereto to obtain a volume of 10 μl, then the mixture was incubated at 37° C. for one hour. Water (40 μl) was added to the incubated mixture, which was extracted with an equal amount of phenol-chloroform. An equal amount of 4M ammonium acetate and twice the volume of ethanol were added to the aqueous layer, which was separated by centrifugation, and thereafter allowed to stand at $-70°$ C. for 15 mins. 67 mM Tris-HCl (pH 8.8), 6.7 mM $MgCl_2$, 16.6 mM ammonium sulfate, 10 mM 2-mercaptoethanol, 6.7 μM EDTA, 0.167% BSA, and 750 μM aliquots of dATP, dGTP, dCTP, dTTP and T4 DNA polymerase (Takara Shuzo Co.) (4 units) were added to the precipitate obtained by centrifugation at 15,000 rpm for 15 mins. The mixture was increased to a total volume of 12 μl and incubated at 37° C. for one hour. The reaction mixture was extracted with an equal amount of phenol-chloroform. The ethanol precipitate was collected by centrifugation and dried in vacuo. EcoRI linker DNA (1 μg) was mixed with 50 mM Tris-HCl (pH 7.6), 10 mM $MgCl_2$, 10 mM dithiothr spermidine, 0.1 mM EDTA, 1 mM ATP and T4 polynucleotide kinase (3 units) (Takara Shuzo Co.) in a volume of 10 μl and the mixture was incubated at 37° C. for 30 mins. The total volume of this mixture was added to the sample which was treated previously with T4 DNA polymerase, T4 ligase (60 units) (Pharmacia Co.) was added, and then the mixture was reacted at 14° C. overnight.

100 mM NaCl, 50 mM Tris-HCl (pH 7.5), 10 mM $MgCl_2$, 7 mM 2-mercaptoethanol, 100 μg/ml BSA and EcoRI (250 units) were added to the reaction mixture, and the total volume was increased to 40 μl then the mixture was incubated at 37° C. for two hours. The reaction mixture was fractionated in 1% low melting point agarose gel and a gel fragment containing 600–2000 pair DNA was collected. After melting the gel at 65° C. for 10 mins., an equal amount of phenol was added thereto; the mixture was subjected to ice cooling for 10 mins., then centrifuged at 4° C. for 10 mins. at 15,000 rpm. An equal amount of phenol was added to the aqueous layer, and the above operations were repeated, thereafter the phenol treatments were again repeated. 1/10 volume 3M sodium acetate and 2.5 volume of ethanol were added to the aqueous layer which had been previously treated with chloroform, and the mixture was allowed to stand at $-70°$ C., then centrifuged at 15,000 rpm for 15 mins. The precipitate, washed twice with 75% ethanol, was dried in vacuo. EcoRI digested λgt11 arms (Stratagene Co. 1 μg) were added thereto and the mixture was subjected to ligation using a ligation kit (Takara Shuzo Co.) at 26° C. for 10 mins. Thereafter a sample was packaged with an in vitro packaging kit (Stratagene Co.) into infectious phage particles. The thus obtained λ phage was infected in *Escherichia coli* LE 392 which was titered at a total of $8.0 \times 10^5$ pfu (plaque forming units).

EXAMPLE 3

The prepared human liver c-DNA library $8.0 \times 10^5$ pfu was inoculated with an indicator bacterium *E. coli* LE 392 (Stratagene Co.) on a medium of 1.5% LB agar medium (bactotrypton 10g, bactoyeast extract 5g and NaCl 10g in 1 l) GSHPx clone was selected by plaque hybridization as previously described. Lytic plaques on the LB plate were transferred to a nylon membrane, which was then contacted with 0.5M NaOH and 1.5M NaCl for 5 mins. and 3M sodium acetate (pH 5.5) for 5 mins., and dried at 80° C. for two hours in vacuo. The membrane was put into a plastic bag, and treated with (10 ml) 5×SSC [1×(150 mM NaCl and 15 mM sodium citrate)], 5 x Denhart solution (0.002% Ficoll, 0.02% polyvinylpyrrolidone and 0.022% BSA), 50 mM sodium phosphate (pH 6.5), 0.1% SDS, 250 μg/ml salmon sperm DNA and 50% formamide at 42° C. for 60 mins. After removing the liquid mixture, synthetic oligonucleotide, in which the 5'-terminal was labelled with 32P ($10^8$ cpm/μg), 5'G T T C A T C T C G G T G T A G T C C C G G A T C G T G G T G C C T C A G A G A G A C G C G A C A T T C T C A A T A G C A G C A C C T T G C C C C G C A G G G A 3' which is a base sequence coding for the amino acid sequence, Ser, Leu, Arg, Gly, Lys, Val, Leu, Leu, Ile, Glu, Asn, Val, Ala, Ser, Leu, Sec, Gly, Thr, Thr, Ile, Arg, Asp, Tyr, Thr, Glu, Met, Asn containing a region coding selenocystein of mouse GSHPx, 20 mg), was added thereto and the mixture was hybridized at 42° C. overnight. The filter was washed three times with 2×SSC and 0.1% SDS at room temperature and at 50° C. for 10 mins., then washed with 0.1×SSC and 0.1% SDS at 50° C. for 10 mins., dried with aeration and autoradiographed. Plaques which showed hybridization with the $^{32}$P-labeled probe on the autoradiograph were collected, diluted with SM [0.1M NaCl, 8 mM MgSO$_4$ and 50 mM Tris-HCl (pH 7.5) and 0.01% gelatin], then again spread on the LB plate. The plaques were selectively purified with the same probe hereinabove for screening, and thus 10 clones were obtained.

EXAMPLE 4

A recombinant λ phase obtained in Example 3 was infected in the host cell LE 392 and cultured with shaking in LB medium (10 ml) overnight. The cultured medium was centrifuged at 8,000 rpm for 10 mins. DNase I (Takara Shuzo Co.) (60 units) and RNase A (Sigma Co.) (100 μg) were added to the supernatant solution and the mixture was incubated at 37° C. for 30 mins. An equal amount of 20% polyethylene glycol and 2.5M NaCl were added thereto, and the mixture was incubated on ice for an hour and centrifuged at 15,000 rpm for 20 mins. The precipitate was suspended in 0.5 ml SM, treated with an equal amount of phenol and centrifuged. The aqueous layer was treated with chloroform-phenol, then 1/10 volume of sodium acetate and 2 volumes of ethanol were added and the mixture was allowed to stand at −70° C. for 15 mins. A precipitate collected by centrifugation at 15,000 rpm for 1 was washed twice with 75% ethanol and dried in vacuo. The precipitate was dissolved in water (50 μl) containing 5 μg/ml RNase A. Complete digestion of the inserted fragment in a solution (10 μl) with EcoRI removed the entire h-GSHPx DNA fragment of approximately 1kb which was fractionated by electrophoresis in a 1% low melting point agarose gel. The fragment of approximately 1kb was recovered from the low melting point agarose gel.

Separately a vector pUC 118 was completely digested with EcoRI, treated with bacterial alkalinephosphatase (0.5 unit) (Toyobo Co.) in 50 mM Tris-HCl (pH 8.0), and incubated at 65° C. for one hour. The reaction mixture was treated twice with chloroform-phenol, 1/10 volume of 3M sodium acetate and 2 volumes of ethanol were added to the aqueous layer, and the material was centrifuged to collect the vector. The inserted fragment recovered from the gel and the vector pUC 118 digested with EcoRI were ligated using a ligation kit (Takara Shuzo Co.)

Logarithmic growth E. coli MV 1304 (Takara Shuzo Co.) cultured in Ψ medium (bactotriptone 20g, bactoyeast extract 5g and MgSO4 14g, in 1 l, pH 7.6) (100 ml) was collected, suspended in an ice cooled solution (40 ml, pH 5.8) of 30 mM potassium acetate, 100 mM RbCl, 10 mM CaCl$_2$, 50 mM MnCl$_2$ and 15% glycerol, and allowed to stand at 0° C. for 5 mins. The bacterial cells were collected by centrifugation, suspended in a solution (4 ml, pH 6.5) of 10 mM MOPS buffer (Dotai Co.), 75 mM CaCl$_2$, 10 mM RbCl and 15% glycerol, and allowed to stand at 0° C. for 15 mins. to allow the cells to become competent. The ligated DNA solution (20 μl) hereinabove was added to the E. coli suspension (200 μl), and the mixture was allowed to stand at 0° C. for 30 mins. The suspension was heated at 42° C. for 90 seconds, LB medium (800 μl) was added thereto, and the material was incubated at 37° C. for 60 mins. The incubated suspension (300 μl) was spread on an LB agar plate containing ampicillin 50 μg/ml, 0.02% X-gel (5-bromo-4-chloro-3-indolyl-β-galactoside) and 50 μM IPTG (isopropyl-β-D-thiogalactopyranoside), then cultured overnight to obtain the transformant. Single white transformant colonies were cultured separately in LB medium (2 ml) overnight and collected by centrifugation. A solution (0.6 ml) of 50 mM Tris-HCl (pH 8.0), 50 mM EDTA (pH 8.0) and 15% sucrose, containing 1 mg/ml lysozyme (Sigma Co.) was added to the collected cells and the material was incubated at 37° C. for 15 mins. 10% SDS (12 μl) was mixed therewith, 5M potassium acetate was added therein and the material was allow to stand at 0° C. for 30 mins. The reaction mixture was centrifuged at 15,000 rpm for 10 mins. The upper layer was treated with an equal amount of chloroform-phenol, then the aqueous layer was treated twice with ether, 2 volumes of ethanol were added, and the mixture was allowed to stand at −70° C. for 15 mins. A precipitate collected by centrifugation at 15,000 rpm for 15 mins. was washed twice with 75% ethanol and dried in vacuo. The precipitate dissolved in water containing 5 μg/ml RNase, was digested with EcoRI and analyzed to select the clone containing the insertion fragment.

EXAMPLE 5

The single colony containing the clone hereinabove was cultured at 37° C. overnight in LB medium (6 ml), and the cultured medium (5 ml) was inoculated in LB medium (500 ml) and cultured at 37° C. Chloramphenicol (20 μl/ml) was added to the cells at logarithmic growth phase and the material was further cultured overnight. Lysozyme dissolved (10 mg/ml) (1.5 ml) in a solution (15 ml) of 8% sucrose, 10% Triton-X, 25 mM EDTA, 50 mM Tris-HCl (pH 8.0) and 0.25 M, Tris-HCl (pH 8.0), was added to the cells collected by centrifugation at 6,000 rpm for 10 mins. and the material was heated to lysate. As supernatant solution obtained by centrifugation at 14,000 rpm for 30 mins. was treated with an equal amount of chloroform-phenol, and 1/10 volume of 3M sodium acetate and 2 volumes of ethanol were added to the aqueous layer, which was then allowed to stand at −70° C. for 15 mins. A precipitate collected by centrifugation at 3,000 rpm for 15 mins. was dissolved in Tris-HCl (pH 7.4) (21 ml), Cesium chloride (20 g) and 10 mg/ml ethidium bromide (1 ml) were added thereto and the mixture was centrifuged at 50,000 rpm and allowed to stand at 4° C. overnight. Closed circular plasmid DNA was fractionated and treated three times with an equal amount of butanol to remove ethidium bromide. The DNA sample was gelfiltered through CL4B Sepharose gel (Pharmacia Co.) washed with Tris-HCl (pH 7.4) containing 0.2M NaCl to remove impurities; 2 volumes of ethanol were added thereto, and the mixture was allowed to stand at −70° C. for 15 mins. As precipitate collected by centrifugation at 3,000 rpm for 30 mins. was washed twice with 75% ethanol, dried and adjusted to concentration of 1 μg/μl.

Single strand DNA of each strand was prepared and the base sequence determined by the dideoxy method [Science, 214: 1205–1210 (1981)]. (FIG. 3)

This plasmid (0.5 μg) was then transformed into E. coli DH1 competent cells (provided by National Institute of Genetics, Japan), which was treated the same as the above E. coli MV 1304, and was inoculated in LB agar medium containing ampicillin 50 μg/ml, then cultured overnight to obtain the transformant. This plasmid containing the human GSHPx gene was designated as *Escherichia coli* DHI pUC 118-GPA.

EXAMPLE 6

EcoRI (15 units) was added to pUC 118-GPA DNA (10 μg) in H-buffer [Maniatis, et al. Molecular Cloning, 104: Cold Spring Harbor (1982)], in a total volume of 20 μl and subjected to cleavage at 37° C. for two hours. DNA fragments of approximately 990 base pairs were extracted from a 1% low melting point agarose gel after electrophoresis, and were purified and dried.

Separately, Bluescript KS (Stratagene Co.) DNA (1 μg) in H-buffer described hereinbefore was mixed with EcoRI to a total volume of 20 μl and cleaved at 37° C. for 2 hours. IM Tris-HCl (pH 8.0) (5 μl) and distilled water (75 μl) were added to the reaction mixture, and the mixture was treated with bacterial alkali phosphate (1 unit) at 65° C. for one hour (hereinafter this treatment with alkali phosphatase is designated BAP-treatment).

DNA was recovered, after twice being treated with an equal amount of chloroform-phenol, by ethanol precipitation, and by being dried in vacuo.

The 990 base pair DNA fragment and BAP treated vector were dissolved in water (17 μl) and ten times concentration of ligation buffer (2 μl) and T4 DNA ligase (Takara Shuzo Co., 350 U/μl) (1 μl) were added thereto; then the mixture was allowed to stand at 14° C. overnight.

The DNA solution reacted as hereinabove was added to the competent *E. coli* D-1 (200 μl), and the mixture was allowed to stand at 0° C. for 30 mins., then at 42° C. for 90 seconds; L-medium (800 μl) was added thereto and the mixture was incubated at 37° C. for 60 mins. The incubated mixture (100 μl) was spread on L-agar medium contining ampicillin 50 μg/ml and was incubated at 37° C. overnight to obtain the transformant. The thus-obtained clone was designated Bluescript KS-GPA.

The Bluescript KS-GPA DNA (10 μg) was added to Hind III (15 units) and BamHI (15 units) in a total volume of 20 μl with H-buffer, and subjected to cleavage at 37° C. for two hours. DNA fragments of approximately 1,000 base pairs were extracted from a 1% low melting point agarose gel after electrophoresis, and were purified and dried.

Separately therefrom, Hind III (2 units) and Bgl II (2 units) were added to pSV2-dhfr DNA (BRL Co.) (1 μg) in a total volume of 20 μl with added H-buffer, then the mixture was subjected to cleavage at 37° C. for two hours, thereafter the mixture was subjected to BAP-treatment to obtain the vector.

The thus-obtained vector and approximately 1,000 base pairs DNA fragment were ligated, transformed into a suitable host and the transformant containing pSV2-GPA was used to prepare large quantities of plasmid DNA. The pSV2-GPA DNA (10 μg) was mixed with EcoRI (15 units) in a volume of 20 μl with added H-buffer and the material wa reacted to cleave at 37° C. for two hours. A DNA fragment of approximately 2,970 base pairs was extracted from 1% low melting point agarose gel after electrophoresis, and dried.

Separately therefrom, EcoRI (2 units) was added to pSV2-dhfr DNA (1 μg) in H-buffer in a total volume of 20 μl, and the mixture was reacted to cleave at 37° C. for two hours. Thus a vector was obtained by BAP-treatment.

Figure 4:
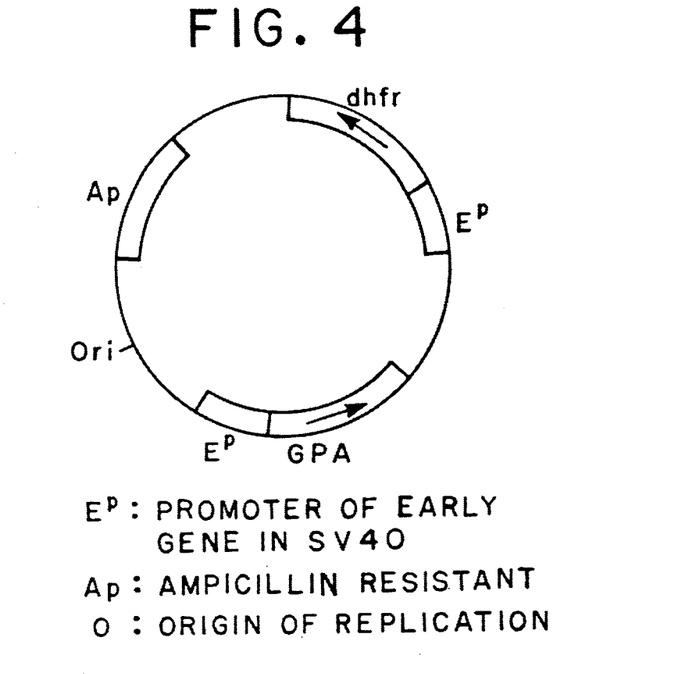
FIG. 4: structural construction of plasmid pSV2-GPA-dhfr.

The said vector and the DNA fragment of approximately 2,970 base pairs were subjected to ligation and transformation. The thus-obtained transformant was designated pSV2-GPA-dhfr. (FIG. 4)

EXAMPLE 7

A solution B consisting of an aqueous solution (2.2 ml) of pSV2-GPA-dhfr DNA (100 μg) and 2M $CaCl_2$ (0.3 ml) was gradually added dropwise with aeration into a solution A consisting of 2×HBS (HEPES 10 g/l, and NaCl 6 g/l, pH 7.10) (2.5 ml) and 100×PO4 (70 mM $NaH_2PO_4$ +70 mM $Na_2HPO_4$) (0.05 ml) to precipitate DNA-calcium phosphate. The said solution of the precipitate (1 ml) was added to CHO-dhfr-cells grown in HamF-12 medium (Flow Co.) containing fetal bovine serum 10% (10 ml) then the material was allowed to stand at 37° C. overnight under a 5% $CO_2$ atmosphere. The culture medium was replaced with fresh medium (10 ml) and the material was incubated further for 24 hours. Finally the medium was changed to D-MEM medium (Gibco Co.) containing dialyzed fetal bovine serum 10% with selection medium, which was changed once every four days, and incubated for one month to obtain transformant cells strain CHO-GPA.

The thus-obtained transformant oells strain CHO-GPA were incubated in D-MEM medium containing fetal bovine serum 0% which contains methotrexate (Sigma Co.) 1 mM, 10 mM and 00 mM, respectively, then the medium was changed once each four days and incubated for one month to obtain the transformant CHO-GPA 100 which can be grown in 100 mM methotrexate.

EXAMPLE 8

The CHO-GPA 100 strain was incubated in D-MEM medium containing fetal bovine serum 10% and 0.02 μM selenious acid and 100 mM methotrexate using a plastic petri dish, diameter 10 cm, 50 plates for three days. The incubated cells, approximately $10^8$ cells, were suspended in 0 mM phosphate buffer (pH 7.0) (100 ml) containing 0.7 mM 2-mercaptoethanol (100 ml) and ultrasonicated. The sonicate was centrifuged at 10,000 rpm for 15 mins. Ammonium sulfate was added to the supernatant enzyme solution, and the precipitate with 25%-50% ammonium sulfate saturation was collected by centrifugation at 15,000 rpm for 30 mins. The precipitate was again dissolved in 10 mM phosphate buffer (pH 7.2) (10 ml) containing 0.7 mM mercaptoethanol and dialyzed three times against 50 volumes of the same buffer solution. The dialyzate was adsorbed on a column (2.5×20 cm) of DEAE-cellulose DE 52 (Whatman Co.) and subjected to gradient elution with a linear gradient of 0-100 mM NaCl in the same buffer solution. Active fractions eluted with NaCl concentration 45-75 mM were collected and concentrated, and subjected to molecular sieving with Sephadex G-200 (Pharmacia Co.) to obtain the enzymatically active fraction.

Figure 5:
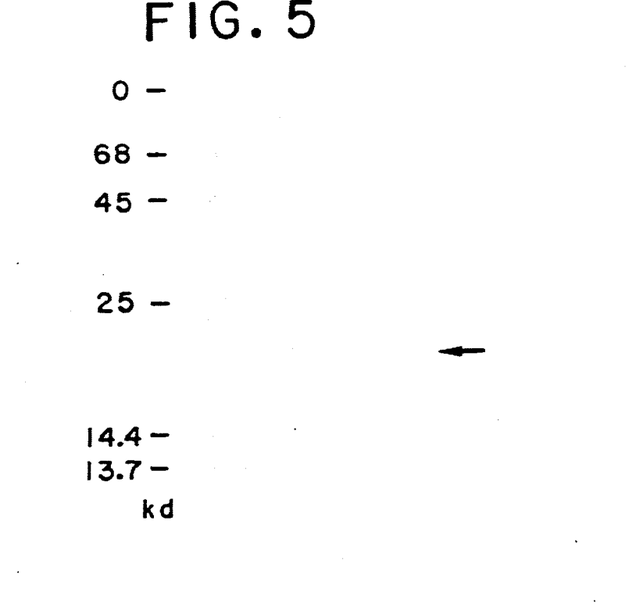
FIG. 5: electrophoresis pattern of purified glutathione peroxidase o the present invention.

The said active fraction was adsorbed on a column (1.5×10 cm) of DEAE-Sephadex (Pharmacia Co.) and eluted with 5 mM phosphate buffer (pH 7.0) containing 0.7 mM 2-mercaptoethanol with a linear gradient of 0-100 mM NaCl concentration. The enzyme active fractions eluted within NaCl concentration 10-20 mM were dialyzed three times against 50 volumes of the same buffer solution, then concentrated to obtain a h-GSHPx specimen. The total protein of this specimen was determined by the Lowry method [J. Biol. Chem. 193: 263-275 (1951)] to obtain 110 μg GSHPx. A comparison was made, of the said sample (1 μg) and standard proteins for reference, namely, bovine serum albumin (68 kDa), egg albumin (45 kDa), chymotrypsinogen (24 kDa), lysozyme (14.4 kDa) and RNAase A (13.7 kDa), each 5 μg, which were treated with 0.1% SDS and 0.5 M 2-mercaptoethanol at 95° C. for 2 mins. These proteins were subjected to SDS-polyacrylamide electrophoresis according to the Laemmli method [Nature, 227: 680–685 (1970)]. The obtained h-GSHPx showed a single band of molecular weight approximately 21 kDa. (FIG. 5)

The h-GSHPx (0.1 μg) was mixed with a solution (0.98 ml) consisting of 0.1 M Tris-HCl (pH 8.0), 0.2 mM reduced NADP, 0.5 mM EDTA, 2 mM glutathione and glutathione reductase (1 unit) Sigma Co.), to which was added t-butyl hydroperoxide (10 μl) (final concentration 70 μM) and the material was incubated at 37° C.

A decrease in absorption at 340 nm of reduced NADP by oxidation was measured. The activity thereof was measured as 0.1 unit, on the condition that an activity that converts 1μ mole of glutathione to oxidized form at 37° C. in one minute, is defined as one unit.

An amino acid sequence of the sample (10 μg) of h-GSHPx of the present invention from N-terminal amino acid was determined in 0.01 M SDS solution by an 890 ME sequencer (Beckman Co.)

The sequence was determined as follows:

Ala—Phe—Ile—Ala—Lys—Ser—Phe—Tyr—Asp—
   Leu—Ser—Ala—Ile—Ser—Leu—Asp—Gly—Glu—Lys—Val.

The above amino acid sequence was identical with the amino acid sequence coded within the plasmide pUC 118-GPA of the present invention.

It will thus be seen that glutathione peroxidase can be effectively produced by DNA and transformants of the present invention. Also an amino acid sequence of a novel glutathione peroxidase from human origin is elucidated according to the present invention, and has been isolated in pure form. A novel form of the glutathione peroxidase gene was also clearly elucidated.

What is claimed is:

1. A recombinant DNA molecule which encodes at least a polypeptide containing glutathione peroxidase activity and having an amino acid sequence from the N-terminal to the C-terminal of the formula:

Ala—Phe—Ile—Ala—Lys—Ser—Phe—Tyr—Asp—Leu—Ser—

—Ala—Ile—Ser—Leu—Asp—Gly—Glu—Lys—Val—Asp—

—Phe—Asn—Thr—Phe—Arg—Gly—Arg—Ala—Val—Leu—

—Ile—Glu—Asn—Val—Arg—Ser—Leu—***—Gly—Thr—Thr—

—Thr—Arg—Asp—Phe—Thr—Gln—Leu—Asn—Glu—Leu—

—Gln—Cys—Arg—Phe—Pro—Arg—Arg—Leu—Val—Val—

—Leu—Gly—Phe—Pro—Cys—Asn—Gln—Phe—Gly—His—

—Gln—Glu—Asn—Cys—Gln—Asn—Glu—Glu—Ile—Leu—

—Asn—Ser—Leu—Lys—Tyr—Val—Arg—Pro—Gly—Gly—

—Gly—Tyr—Gln—Pro—Thr—Phe—Thr—Leu—Val—Gln—

—Lys—Cys—Glu—Val—Asn—Gly—Gln—Asn—Glu—His—

—Pro—Val—Phe—Ala—Tyr—Leu—Lys—Asp—Lys—Leu—

—Pro—Tyr—Pro—Tyr—Asp—Asp—Pro—Phe—Ser—Leu—

—Met—Thr—Asp—Pro—Lys—Leu—Ile—Ile—Trp—Ser—Pro—

—Val—Arg—Arg—Ser—Asp—Val—Ala—Trp—Asn—Phe—

—Glu—Lys—Phe—Leu—Ile—Gly—Pro—Glu—Gly—Glu—

—Pro—Phe—Arg—Arg—Tyr—Ser—Arg—Thr—Phe—Pro—

—Thr—Ile—Asn—Ile—Glu—Pro—Asp—Ile—Lys—Arg—Leu—

—Leu—Lys—Val—Ala—Ile wherein * * * is selenocystein.

2. DNA according to claim 1 of a sequence of at least 567 nucleotides as shown in FIG. 2.

3. A transformant comprising a DNA sequence heterologous to the host DNA according to claim 1.

4. A transformant according to claim 3 wherein the heterologous DNA sequence is of at least the 567 base pairs of FIG. 2.

5. A transformant according to claim 3 which is eukaryotic or prokaryotic.

6. A polypeptide with glutathione peroxidase activity having the amino acid sequence shown in claim 1.

7. A process for the production of glutathione peroxidase which comprises culturing transformant host cells which comprise heterologous DNA according to claim 1, said DNA encoding a polypeptide with glutathione peroxidase activity in a medium containing selenium, and separating a thus-produced polypeptide with glutathione peroxidase activity from the cultured mass.

8. A process according to claim 7 wherein the said transformant host cells are bacteria or Saccharomyces or animal cells.

* * * * *